US006939673B2

(12) United States Patent
Bass et al.

(10) Patent No.: US 6,939,673 B2
(45) Date of Patent: Sep. 6, 2005

(54) MANUFACTURE OF ARRAYS WITH REDUCED ERROR IMPACT

(75) Inventors: Jay K. Bass, Mountain View, CA (US); Maryam Mobed-Miremadi, Sunnyvale, CA (US); Eric M. Leproust, Campbell, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 232 days.

(21) Appl. No.: 10/172,468

(22) Filed: Jun. 14, 2002

(65) Prior Publication Data

US 2003/0232123 A1 Dec. 18, 2003

(51) Int. Cl.[7] .......................... C07H 21/04; C12Q 1/68
(52) U.S. Cl. .................. 435/6; 435/91.1; 435/91.2; 435/287.2; 536/23.1; 536/24.3
(58) Field of Search .................. 435/6, 91.1, 91.2, 435/287.1; 536/23.1

(56) References Cited

U.S. PATENT DOCUMENTS

| 5,922,534 A | 7/1999 | Lichtenwalter |
| 5,981,733 A | 11/1999 | Gamble et al. |
| 6,001,309 A | 12/1999 | Gamble et al. |
| 6,140,044 A | 10/2000 | Besemer et al. |
| 6,558,623 B1 | 5/2003 | Ganz et al. |

FOREIGN PATENT DOCUMENTS

| GB | 2355716 A | 4/2000 |
| WO | WO 00/34523 | 6/2000 |
| WO | WO 00/60425 | 10/2000 |

OTHER PUBLICATIONS

U.S. Appl. No. 09/302,898, filed Apr. 30, 1999, Caren et al.
U.S. Appl. No. 09/359,527, filed Jul. 22, 1999, Web et al.

Primary Examiner—Jeanine A. Goldberg
(74) Attorney, Agent, or Firm—Agilent Technologies, Inc.

(57) ABSTRACT

Methods and apparatus are disclosed for synthesizing a purality of compounds such as biopolymers on the surface of supports. The synthesis comprises a plurality of steps in which reagents for conducting the synthesis are deposited o the surface of the support to form precursors of the chemical compounds and, ultimately, the chemical compounds themselves. An error in the deposition may occur in one or more of the plurality of steps. A reagent for forming the chemical compounds is deposited on the surface of the support. A determination is made as to whether an error occurred in the depositing of the reagent. If an error is detected, the support is treated to re-deposit at least some of those reagents that were not correctly deposited. In one approach the support is treated to stabilize precursors of the chemical compounds, the source of the error is corrected, and the reagent applied above is re-deposited on the surface.

6 Claims, 3 Drawing Sheets

MANUFACTURE OF ARRAYS WITH REDUCED ERROR IMPACT

BACKGROUND OF THE INVENTION

This invention relates to the manufacturing of supports having bound to the surfaces thereof a plurality of chemical compounds such as polymers, which are prepared on the surface in a series of steps. More particularly, the present invention relates to methods for solid phase chemical synthesis, particularly solid phase synthesis of oligomer arrays, or attachment of oligonucleotides and polynucleotides to surfaces, e.g., arrays of polynucleotides, where reagents are delivered as droplets to the surface of a support.

In the field of diagnostics and therapeutics, it is often useful to attach species to a surface. One important application is in solid phase chemical synthesis wherein initial derivatization of a substrate surface enables synthesis of polymers such as oligonucleotides and peptides on the substrate itself. Support bound oligomer arrays, particularly oligonucleotide arrays and polypeptide arrays, may be used in screening studies for determination of binding affinity. Modification of surfaces for use in chemical synthesis has been described. See, for example, U.S. Pat. No. 5,624,711 (Sundberg), U.S. Pat. No. 5,266,222 (Willis) and U.S. Pat. No. 5,137,765 (Farnsworth).

Determining the nucleotide sequences and expression levels of nucleic acids (DNA and RNA) is critical to understanding the function and control of genes and their relationship, for example, to disease discovery and disease management. Analysis of genetic information plays a crucial role in biological experimentation. This has become especially true with regard to studies directed at understanding the fundamental genetic and environmental factors associated with disease and the effects of potential therapeutic agents on the cell. Such a determination permits the early detection of infectious organisms such as bacteria, viruses, etc.; genetic diseases such as sickle cell anemia; and various cancers. This paradigm shift has lead to an increasing need within the life science industries for more sensitive, more accurate and higher-throughput technologies for performing analysis on genetic material obtained from a variety of biological sources.

Unique or misexpressed nucleotide sequences in a polynucleotide can be detected by hybridization with a nucleotide multimer, or oligonucleotide, probe. Hybridization is based on complementary base pairing. When complementary single stranded nucleic acids are incubated together, the complementary base sequences pair to form double stranded hybrid molecules. These techniques rely upon the inherent ability of nucleic acids to form duplexes via hydrogen bonding according to Watson-Crick base-pairing rules. The ability of single stranded deoxyribonucleic acid (ssDNA) or ribonucleic acid (RNA) to form a hydrogen bonded structure with a complementary nucleic acid sequence has been employed as an analytical tool in molecular biology research. An oligonucleotide probe employed in the detection is selected with a nucleotide sequence complementary, usually exactly complementary, to the nucleotide sequence in the target nucleic acid. Following hybridization of the probe with the target nucleic acid, any oligonucleotide probe/nucleic acid hybrids that have formed are typically separated from unhybridized probe. The amount of oligonucleotide probe in either of the two separated media is then tested to provide a qualitative or quantitative measurement of the amount of target nucleic acid originally present.

Direct detection of labeled target nucleic acid hybridized to surface-bound polynucleotide probes is particularly advantageous if the surface contains a mosaic of different probes that are individually localized to discrete, known areas of the surface. Such ordered arrays containing a large number of oligonucleotide probes have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations. The arrays may be used for conducting cell study, for diagnosing disease, identifying gene expression, monitoring drug response, determination of viral load, identifying genetic polymorphisms, analyze gene expression patterns or identify specific allelic variations, and the like.

In one approach, cell matter is lysed, to release its DNA as fragments, which are then separated out by electrophoresis or other means, and then tagged with a fluorescent or other label. The resulting DNA mix is exposed to an array of oligonucleotide probes, whereupon selective binding to matching probe sites takes place. The array is then washed and interrogated to determine the extent of hybridization reactions. In one approach the array is imaged so as to reveal for analysis and interpretation the sites where binding has occurred. Arrays of different chemical probe species provide methods of highly parallel detection, and hence improved speed and efficiency, in assays. Assuming that the different sequence polynucleotides were correctly deposited in accordance with the predetermined configuration, then the observed binding pattern will be indicative of the presence and/or concentration of one or more polynucleotide components of the sample.

Biopolymer arrays can be fabricated using either in situ synthesis methods or deposition of the previously obtained biopolymers. The in situ synthesis methods include those described in U.S. Pat. No. 5,449,754 for synthesizing peptide arrays, as well as WO 98/41531 and the references cited therein for synthesizing polynucleotides (specifically, DNA). Such in situ synthesis methods can be basically regarded as iterating the sequence of depositing droplets of: (a) a protected monomer onto predetermined locations on the surface of a support to link with either a suitably activated surface or with a previously deposited deprotected monomer; (b) deprotecting the deposited monomer so that it can now react with a subsequently deposited protected monomer; and (c) depositing another protected monomer for linking. Different monomers may be deposited at different regions on the substrate during any one iteration so that the different regions of the completed array will have different desired biopolymer sequences. One or more intermediate steps may be required in each iteration such as, for example, capping or blocking, oxidation, deprotection of protection groups or deblocking, and washing steps.

In the deposition methods biopolymers are deposited at predetermined locations on a support surface that is suitably activated such that the biopolymers can become linked to the surface. Biopolymers of different sequence may be deposited at different regions of the substrate to yield the completed array. Washing or other additional steps may also be used.

Typical procedures are known in the art for deposition of polynucleotides, particularly DNA such as whole oligomers or cDNA. One such procedure involves loading a small volume of DNA in solution in one or more drop dispensers such as the tip of a pin or in an open capillary and touching the pin or capillary to the surface of the substrate. Such a procedure is described in U.S. Pat. No. 5,807,522. When the fluid touches the surface, some of the fluid is transferred. The pin or capillary must be washed prior to picking up the next type of DNA for spotting onto the array. This process is repeated for many different sequences and, eventually, the desired array is formed.

In another approach reagents for in situ synthesis or DNA can be loaded into a drop dispenser in the form of an inkjet head and fired onto the surface of the support. Such a technique has been described, for example, in PCT publications WO 95/25116 and WO 98/41531, and elsewhere. This method has the advantage of non-contact deposition. Other methods involve pipetting apparatus and positive displacement pumps such as, for example, the Biodot equipment available from Bio-Dot Inc., Irvine Calif., USA.

In array fabrication, there may be instances where an error occurs during the deposition of reagents on the surface of a support. Such errors may result, for example, from non-delivery of reagent from one or more of dispensing elements such as the dispensing nozzles of an inkjet apparatus. Errors of this kind basically render the support non-usable because one or more of the biopolymers deposited on the surface are incorrect. In instances of error occurrence, the particular synthesis is stopped, the support is discarded, the source of the error, e.g., clogged printing nozzle, is fixed and a new synthesis is carried out with a new support starting from the beginning of the synthetic procedure. As may be appreciated, the occurrence of an error gives rise to a considerable amount of lost time, material and reagents.

There is a need, therefore, for a method for fabricating arrays such that errors that occur during the deposition of reagents on a support are detected; the source of the error is repaired; the error itself is corrected; and the fabrication is resumed with the same support.

SUMMARY OF THE INVENTION

One embodiment of the present invention is a method for synthesizing an array of chemical compounds on the surface of a support. The synthesis comprises a plurality of steps in which reagents for conducting the synthesis are deposited on the surface of the support to form precursors of the chemical compounds. One or more of the plurality of steps may comprise an error in the deposition. Reagents for forming the chemical compounds are deposited on multiple locations on the surface. The above step is repeated in one or more cycles so as to form the chemical compounds. The reagents deposited in different cycles at the same locations on the surface may or may not be the same. The method additionally comprises in at least one selected cycle determining whether an error occurred in the depositing of the first reagents in the selected cycle. If an error occurred, the source of the error is corrected and at least some of those of the reagents that were not correctly deposited in the selected cycle are re-deposited on the surface. Optionally, the support may be treated to stabilize precursors of the chemical compounds after an error is detected.

Another embodiment of the present invention is a method for synthesizing an array of biopolymers on the surface of a support. A plurality of steps is employed in the synthesis wherein reagents comprising biopolymer subunits are deposited on multiple locations on the surface of the support. During the deposition an error may occur in one or more of the plurality of steps. A support having a functionalized surface is placed into a reaction chamber. A plurality of drops of a reagent comprising a biopolymer subunit is dispensed to the surface from a plurality of nozzles. The above step is repeated in one or more cycles so as to form the biopolymers. A determination is made as to whether an error occurred in the dispensing of the reagent. If an error is detected, the support is removed from the reaction chamber and placed in a holding chamber; the surface of the support in the holding chamber is stabilized; the source of the error is corrected; the support is returned to the reaction chamber; and a plurality of drops of the above reagents is dispensed to the surface from a plurality of nozzles. The normal steps of the synthesis are resumed where again a plurality of drops of a reagent comprising a biopolymer unit is dispensed to the surface from a plurality of nozzles. The above steps are repeated to form the biopolymers of predetermined characteristics.

Another embodiment of the present invention is an apparatus for synthesizing an array of biopolymers on the surface of a support. The apparatus comprises a reaction chamber, a mechanism for moving a support to and from the reaction chamber, a controller for controlling the movement of the aforementioned mechanism, one or more fluid dispensing stations in fluid communication with the reaction chamber, a second mechanism for determining the correct operation of the fluid dispensing stations, and a controller for controlling the second mechanism. The mechanism for determining the correct operation of the fluid dispensing stations is in communication with the controller for controlling the movement of the mechanism for moving a support to and from the reaction chamber. The apparatus further comprises a stabilization chamber for subjecting the support to stabilization reagents. The apparatus may optionally comprise one or more additional chambers for conducting reactions that form part of the synthesis.

Another embodiment of the present invention is a method for synthesizing a plurality of chemical compounds on the surface of a support. The synthesis comprises a plurality of steps in which reagents for conducting the synthesis are deposited on the surface of the support to form precursors of the chemical compounds and, ultimately, the chemical compounds themselves. An error in the deposition may occur in one or more of the plurality of steps. In the method in accordance with the present invention, a reagent for forming the chemical compounds is deposited on the surface of the support. A determination is made as to whether an error occurred in the depositing of the reagent. If an error is detected, then, in accordance with the present invention, the support is treated to re-deposit at least those reagents that were not correctly deposited because of the error in the deposition step. In one approach the support is treated to stabilize precursors of the chemical compounds, the source of the error is corrected, and the reagent applied in the step in which the error was detected is re-deposited on the surface. In an alternative approach, if an error is detected, the error is corrected and the reagents that were not correctly delivered to the surface of the support are dispensed to the surface only at the locations where reagent deposition did not occur because of the error. Subsequent to the aforementioned corrective approaches, the synthesis is continued in its normal pattern wherein a next a reagent for forming the chemical compounds is deposited on the surface. The above steps are repeated to form the chemical compounds.

DETAILED DESCRIPTION OF THE INVENTION

Figure 1:
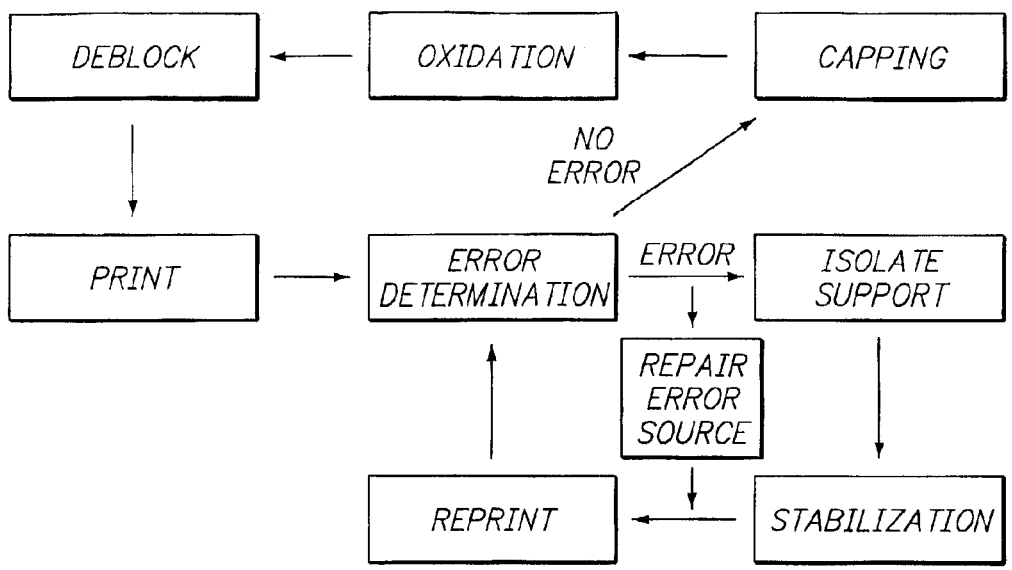
FIG. 1 is a flow chart depicting one embodiment of a method in accordance with the present invention.

The present methods and apparatus may be employed in the synthesis of a plurality of chemical compounds on supports with particular application to such synthesis on a commercial scale. The invention has application to the deposition of reagents for yielding the chemical compounds. Such reagents may be, for example, chemical components for forming the chemical compounds, fully formed chemical compounds that are deposited on a surface, and so forth. Usually, the chemical compounds are those that are synthesized in a series of steps such as, for example, the addition of building blocks, which are chemical components of the chemical compound. Examples of such building blocks include those found in the synthesis of polymers such as, for example, subunits of the polymers.

As mentioned above, the chemical compounds are those that are synthesized in a series of steps, which usually involve linking together building blocks that form the chemical compound. The invention has particular application to the synthesis of oligomers or polymers. The oligomer or polymer is a chemical entity that contains a plurality of monomers. It is generally accepted that the term "oligomers" is used to refer to a species of polymers. The terms "oligomer" and "polymer" may be used interchangeably herein. Polymers usually comprise at least two monomers. Oligomers generally comprise about 6 to about 20,000 monomers, preferably, about 10 to about 10,000, more preferably about 15 to about 4,000 monomers. Examples of polymers include polydeoxyribonucleotides, polyribonucleotides, other polynucleotides that are C-glycosides of a purine or pyrimidine base, or other modified polynucleotides, polypeptides, polysaccharides, and other chemical entities that contain repeating units of like chemical structure. Exemplary of oligomers are oligonucleotides and peptides.

A monomer is a chemical entity that can be covalently linked to one or more other such entities to form an oligomer or polymer. Examples of monomers include nucleotides, amino acids, saccharides, peptoids, and the like and subunits comprising nucleotides, amino acids, saccharides, peptoids and the like. The subunits may comprise all of the same component such as, for example, all of the same nucleotide or amino acid, or the subunit may comprise different components such as, for example, different nucleotides or different amino acids. The subunits may comprise about 2 to about 2000, or about 5 to about 200, monomer units. In general, the monomers have first and second sites (e.g., C-termini and N-termini, or 5' and 3' sites) suitable for binding of other like monomers by means of standard chemical reactions (e.g., condensation, nucleophilic displacement of a leaving group, or the like), and a diverse element that distinguishes a particular monomer from a different monomer of the same type (e.g., an amino acid side chain, a nucleotide base, etc.). The initial substrate-bound, or support-bound, monomer is generally used as a building block in a multi-step synthesis procedure to form a complete ligand, such as in the synthesis of oligonucleotides, oligopeptides, oligosaccharides, etc. and the like.

A biomonomer references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

A biopolymer is a polymer of one or more types of repeating units. Biopolymers are typically found in biological systems and particularly include polysaccharides (such as carbohydrates), and peptides (which term is used to include polypeptides, and proteins whether or not attached to a polysaccharide) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions.

Polynucleotides are compounds or compositions that are polymeric nucleotides or nucleic acid polymers. The polynucleotide may be a natural compound or a synthetic compound. Polynucleotides include oligonucleotides and are comprised of natural nucleotides such as ribonucleotides and deoxyribonucleotides and their derivatives although unnatural nucleotide mimetics such as 2'-modified nucleosides, peptide nucleic acids and oligomeric nucleoside phosphonates are also used. The polynucleotide can have from about 2 to 5,000,000 or more nucleotides. Usually, the oligonucleotides are at least about 2 nucleotides, usually, about 5 to about 100 nucleotides, more usually, about 10 to about 50 nucleotides, and may be about 15 to about 30 nucleotides, in length. Polynucleotides include single or multiple stranded configurations, where one or more of the strands may or may not be completely aligned with another.

A nucleotide refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides.

The support to which a plurality of chemical compounds is attached is usually a porous or non-porous water insoluble material. The support can have any one of a number of shapes, such as strip, plate, disk, rod, particle, and the like. The support can be hydrophilic or capable of being rendered hydrophilic or it may be hydrophobic. The support is usually glass such as flat glass whose surface has been chemically activated to support binding or synthesis thereon, glass available as Bioglass and the like. However, the support may be made from materials such as inorganic powders, e.g., silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly (vinyl butyrate), etc.; either used by themselves or in conjunction with other materials; ceramics, metals, and the like. Preferably, for packaged arrays the support is a non-porous material such as glass, plastic, metal and the like.

The surface of a support is normally treated to create a primed or functionalized surface, that is, a surface that is able to support the synthetic steps involved in the production of the chemical compound. Functionalization relates to modification of the surface of a support to provide a plurality of functional groups on the support surface. By the term "functionalized surface" is meant a support surface that has been modified so that a plurality of functional groups are present thereon. The manner of treatment is dependent on the nature of the chemical compound to be synthesized and on the nature of the support surface. In one approach a reactive hydrophilic site or reactive hydrophilic group is introduced onto the surface of the support. Such hydrophilic moieties can be used as the starting point in a synthetic organic process.

In one embodiment, the surface of the support, such as a glass support, is siliceous, i.e., comprises silicon oxide groups, either present in the natural state, e.g., glass, silica, silicon with an oxide layer, etc., or introduced by techniques well known in the art. One technique for introducing siloxyl groups onto the surface involves reactive hydrophilic moieties on the surface. These moieties are typically epoxide groups, carboxyl groups, thiol groups, and/or substituted or unsubstituted amino groups as well as a functionality that may be used to introduce such a group such as, for example, an olefin that may be converted to a hydroxyl group by means well known in the art. One approach is disclosed in U.S. Pat. No. 5,474,796 (Brennan), the relevant portions of which are incorporated herein by reference. A siliceous surface may be used to form silyl linkages, i.e., linkages that involve silicon atoms. Usually, the silyl linkage involves a silicon-oxygen bond, a silicon-halogen bond, a silicon-nitrogen bond, or a silicon-carbon bond.

Another method for attachment is described in U.S. Pat. No. 6,219,674 (Fulcrand, et al.). A surface is employed that comprises a linking group consisting of a first portion comprising a hydrocarbon chain, optionally substituted, and a second portion comprising an alkylene oxide or an alkylene imine wherein the alkylene is optionally substituted. One end of the first portion is attached to the surface and one end of the second portion is attached to the other end of the first portion chain by means of an amine or an oxy functionality. The second portion terminates in an amine or a hydroxy functionality. The surface is reacted with the substance to be immobilized under conditions for attachment of the substance to the surface by means of the linking group.

Another method for attachment is described in U.S. Pat. No. 6,258,454 (Lefkowitz, et al.). A solid support having hydrophilic moieties on its surface is treated with a derivatizing composition containing a mixture of silanes. A first silane provides the desired reduction in surface energy, while the second silane enables functionalization with molecular moieties of interest, such as small molecules, initial monomers to be used in the solid phase synthesis of oligomers, or intact oligomers. Molecular moieties of interest may be attached through cleavable sites.

A procedure for the derivatization of a metal oxide surface uses an aminoalkyl silane derivative, e.g., trialkoxy 3-aminopropylsilane such as aminopropyltriethoxy silane (APS), 4-aminobutyltrimethoxysilane, 4-aminobutyltriethoxysilane, 2-aminoethyltriethoxysilane, and the like. APS reacts readily with the oxide and/or siloxyl groups on metal and silicon surfaces. APS provides primary amine groups that may be used to carry out the present methods. Such a derivatization procedure is described in EP 0 173 356 B1, the relevant portions of which are incorporated herein by reference. Other methods for treating the surface of a support will be suggested to those skilled in the art in view of the teaching herein. Such methods include, for example, creating hydroxyl terminated surfaces and so forth.

The apparatus and methods of the present invention are particularly useful in the synthesis of arrays of biopolymers. A biopolymer is a polymer of one or more types of repeating units relating to biology. Biopolymers are typically found in biological systems (although they may be made synthetically) and particularly include polysaccharides such as carbohydrates and the like, poly(amino acids) such as peptides including polypeptides and proteins, and polynucleotides, as well as such compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions.

An array includes any one, two or three dimensional arrangement of addressable regions bearing a particular chemical moiety or moieties such as, for example, biopolymers, e.g., one or more polynucleotides, associated with that region. An array is addressable in that it has multiple regions of different moieties, for example, different polynucleotide sequences, such that a region or feature or spot of the array at a particular predetermined location or address on the array can detect a particular target molecule or class of target molecules although a feature may incidentally detect non-target molecules of that feature. Where a predetermined arrangement of arrays is desired, any of a variety of geometries may be constructed. In one approach the array may be in the form of organized rows and columns of features. In alternative approaches, arrays can be arranged in a series of curvilinear rows across the surface of a support such as, for example, a series of concentric circles or semi-circles of spots, and the like.

The present methods and apparatus may be used in the synthesis of polypeptides. The synthesis of polypeptides involves the sequential addition of amino acids to a growing peptide chain. This approach comprises attaching an amino acid to the functionalized surface of the support. In one approach the synthesis involves sequential addition of carboxyl-protected amino acids to a growing peptide chain with each additional amino acid in the sequence similarly protected and coupled to the terminal amino acid of the oligopeptide under conditions suitable for forming an amide linkage. Such conditions are well known to the skilled artisan. See, for example, Merrifield, B. (1986), Solid Phase Synthesis, *Sciences* 232, 341–347. After polypeptide synthesis is complete, acid is used to remove the remaining terminal protecting groups.

The present invention has particular application to the synthesis of arrays of chemical compounds on a surface of a support. Typically, methods and apparatus of the present invention generate or use an array assembly that may include a support carrying one or more arrays disposed along a surface of the support and separated by inter-array areas. Normally, the surface of the support opposite the surface with the arrays does not carry any arrays. The arrays can be designed for testing against any type of sample, whether a trial sample, a reference sample, a combination of the foregoing, or a known mixture of components such as polynucleotides, proteins, polysaccharides and the like (in which case the arrays may be composed of features carrying unknown sequences to be evaluated). The surface of the support may carry at least one, two, four, or at least ten, arrays. Depending upon intended use, any or all of the arrays may be the same or different from one another and each may contain multiple spots or features of chemical compounds such as, e.g., biopolymers in the form of polynucleotides or other biopolymer. A typical array may contain more than ten, more than one hundred, more than one thousand or ten thousand features, or even more than one hundred thousand features, in an area of less than 20 $cm^2$ or even less than 10 $cm^2$. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded, the remaining features may account for at least 5%, 10%, or 20% of the total number of features).

Each feature, or element, within the molecular array is defined to be a small, regularly shaped region of the surface of the substrate. The features are arranged in a predetermined manner. Each feature of an array usually carries a predetermined chemical compound or mixtures thereof. Each feature within the molecular array may contain a different molecular species, and the molecular species within a given feature may differ from the molecular species within the remaining features of the molecular array. Some or all of the features may be of different compositions. Each array may contain multiple spots or features and each array may be separated by spaces or areas. It will also be appreciated that there need not be any space separating arrays from one another. Interarray areas and interfeature areas are usually present but are not essential. These areas do not carry any chemical compound such as polynucleotide (or other biopolymer of a type of which the features are composed). Interarray areas and interfeature areas typically will be present where arrays are formed by the conventional in situ process or by deposition of previously obtained moieties, as described above, by depositing for each feature at least one droplet of reagent such as from a pulse jet (for example, an inkjet type head) but may not be present when, for example, photolithographic array fabrication processes are used. It will be appreciated though, that the interarray areas and interfeature areas, when present, could be of various sizes and configurations.

Each array may cover an area of less than 100 $cm^2$, or even less than 50 $cm^2$, 10 $cm^2$ or 1 $cm^2$. In many embodiments, the support (sometimes referenced as a "substrate") carrying the one or more arrays may be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally, in this situation the substrate may be relatively transparent to reduce the absorption of the incident illuminating laser light and subsequent heating if the focused laser beam travels too slowly over a region. For example, the substrate may transmit at least 20%, or 50% (or even at least 70%, 90%, or 95%), of the illuminating light incident on the front as may be measured across the entire integrated spectrum of such illuminating light or alternatively at 532 nm or 633 nm. Flexible or rigid substrates may be used.

The devices and methods of the present invention are particularly useful in the synthesis of oligonucleotide arrays for determinations of polynucleotides. As explained briefly above, in the field of bioscience, arrays of oligonucleotide probes, fabricated or deposited on a surface of a support, are used to identify DNA sequences in cell matter. The arrays generally involve a surface containing a mosaic of different oligonucleotides or sample nucleic acid sequences or polynucleotides that are individually localized to discrete, known areas of the surface. In one approach, multiple identical arrays across a complete front surface of a single substrate or support are used.

Ordered arrays containing a large number of oligonucleotides have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations. The arrays may be used for conducting cell study, for diagnosing disease, identifying gene expression, monitoring drug response, determination of viral load, identifying genetic polymorphisms, analyze gene expression patterns or identify specific allelic variations, and the like.

The synthesis of arrays of polynucleotides on the surface of a support usually involves attaching an initial nucleoside or nucleotide to a functionalized surface. The surface may be functionalized as discussed above. In one approach the surface is reacted with nucleosides or nucleotides that are also functionalized for reaction with the groups on the surface of the support. Methods for introducing appropriate amine specific or alcohol specific reactive functional groups into a nucleoside or nucleotide include, by way of example, addition of a spacer amine containing phosphoramidites, addition on the base of alkynes or alkenes using palladium mediated coupling, addition of spacer amine containing activated carbonyl esters, addition of boron conjugates, formation of Schiff bases.

After the introduction of the nucleoside or nucleotide onto the surface, the attached nucleotide may be used to construct the polynucleotide by means well known in the art. For example, in the synthesis of arrays of oligonucleotides, nucleoside monomers are generally employed. In this embodiment an array of the above compounds is attached to the surface and each compound is reacted to attach a nucleoside. Nucleoside monomers are used to form the polynucleotides usually by phosphate coupling, either direct phosphate coupling or coupling using a phosphate precursor such as a phosphite coupling. Such coupling thus includes the use of amidite (phosphoramidite), phosphodiester, phosphotriester, H-phosphonate, phosphite halide, and the like coupling.

One preferred coupling method is phosphoramidite coupling, which is a phosphite coupling. In using this coupling method, after the phosphite coupling is complete, the resulting phosphite is oxidized to a phosphate. Oxidation can be effected with iodine to give phosphates or with sulfur to give phosphorothioates. The phosphoramidites are dissolved in anhydrous acetonitrile to give a solution having a given ratio of amidite concentrations. The mixture of known chemically compatible monomers is reacted to a solid support, or further along, may be reacted to a growing chain of monomer units, which may also be referred to as the polymer precursors. In one particular example, the terminal 5'-hydroxyl group is caused to react with a deoxyribonucleoside-3'-O-(N,N-diisopropylamino) phosphor-amidite protected at the 5'-position with dimethoxytrityl or the like. The 5' protecting group is removed after the coupling reaction, and the procedure is repeated with additional protected nucleotides until synthesis of the desired polynucleotide is complete. For a more detailed discussion of the chemistry involved in the above synthetic approaches, see, for example, U.S. Pat. No. 5,436,327 at column 2, line 34, to column 4, line 36, which is incorporated herein by reference in its entirety.

Various ways may be employed to introduce the reagents for producing an array of polynucleotides on the surface of a support such as a glass support. Such methods are known in the art and include methods involving dispensing reagents to the surface of a support in the form of droplets. One in situ method employs inkjet printing technology to dispense the appropriate phosphoramidite reagents and other reagents onto individual sites on a surface of a support. Oligonucleotides are synthesized on a surface of a substrate in situ using phosphoramidite chemistry. Solutions containing nucleotide monomers and other reagents as necessary such as an activator, e.g., tetrazole, are applied to the surface of a support by means of ink-jet technology such as, e.g., thermal ink-jet technology or piezo inkjet technology. Individual droplets of reagents are applied to reactive areas on the surface using, for example, a thermal ink-jet type nozzle or piezo inkjet technology. The surface of the support may have a double bond terminated alkyl trichlorosilane coating, which is reacted in a hydroboration reaction to provide terminal hydroxyl groups. These hydroxyl groups provide for linking to a terminal primary amine group on a monomeric reagent. Excess of non-reacted chemical on the surface is washed away in a subsequent step. For example, see U.S. Pat. No. 5,700,637 and PCT WO 95/25116 and PCT application WO 89/10977.

For in situ fabrication methods, multiple different reagent droplets are deposited on the surface of a support at a given target location in order to form the final feature (hence a probe of the feature is synthesized on the array substrate). Deposition may be by, for example, pulsejet or other similar means. The in situ fabrication methods include those described in U.S. Pat. No. 5,449,754 for synthesizing peptide arrays, and in U.S. Pat. No. 6,180,351 and WO 98/41531 and the references cited therein for polynucleotides, and may also use pulsejets for depositing reagents. The in situ method for fabricating a polynucleotide array typically follows, at each of the multiple different addresses at which features are to be formed, the same conventional iterative sequence used in forming polynucleotides from nucleoside reagents on a support by means of known chemistry.

This iterative sequence can be considered as multiple ones of the following attachment cycle at each feature to be formed: (a) coupling an activated selected nucleoside (a monomeric unit) through a phosphite linkage to a functionalized support in the first iteration, or a nucleoside bound to the substrate (i.e. the nucleoside-modified substrate) in subsequent iterations; (b) optionally, blocking unreacted hydroxyl groups on the substrate bound nucleoside (sometimes referenced as "capping"); (c) oxidizing the phosphite linkage of step (a) to form a phosphate linkage; and (d) removing the protecting group ("deprotection") from the now substrate bound nucleoside coupled in step (a), to generate a reactive site for the next cycle of these steps. The coupling can be performed by depositing drops of an activator and phosphoramidite at the specific desired feature locations for the array. Capping, oxidation and deprotection can be accomplished by treating the entire substrate ("flooding") with a layer of the appropriate reagent. The functionalized support (in the first cycle) or deprotected coupled nucleoside (in subsequent cycles) provides a substrate bound moiety with a linking group for forming the phosphite linkage with a next nucleoside to be coupled in step (a). Final deprotection of nucleoside bases can be accomplished using alkaline conditions such as ammonium hydroxide, in another flooding procedure in a known manner. Conventionally, a single pulsejet or other dispenser is assigned to deposit a single monomeric unit.

Another approach for fabricating an array of biopolymers on a substrate using a biopolymer or biomonomer fluid and using a fluid dispensing head is described in U.S. Pat. No. 6,242,266 (Schleifer, et al.). The head has at least one jet that can dispense droplets onto a surface of a support. The jet includes a chamber with an orifice and an ejector, which, when activated, causes a droplet to be ejected from the orifice. Multiple droplets of the biopolymer or biomonomer fluid are dispensed from the head orifice so as to form an array of droplets on the surface of the substrate.

In another embodiment (U.S. Pat. No. 6,232,072) (Fisher) a method of, and apparatus for, fabricating a biopolymer array is disclosed. Droplets of fluid carrying the biopolymer or biomonomer are deposited onto a front side of a transparent substrate. Light is directed through the substrate from the front side, back through a substrate back side and a first set of deposited droplets on the first side to an image sensor.

An example of another method for chemical array fabrication is described in U.S. Pat. No. 6,180,351 (Cattell). The method includes receiving from a remote station information on a layout of the array and an associated first identifier. A local identifier is generated corresponding to the first identifier and associated array. The local identifier is shorter in length than the corresponding first identifier. The addressable array is fabricated on the substrate in accordance with the received layout information.

The foregoing chemistry of the synthesis of polynucleotides is described in detail, for example, in Caruthers, *Science* 230: 281–285, 1985; Itakura, et al., *Ann. Rev. Biochem.* 53: 323–356; Hunkapillar, et al., *Nature* 310: 105–110, 1984; and in "Synthesis of Oligonucleotide Derivatives in Design and Targeted Reaction of Oligonucleotide Derivatives", CRC Press, Boca Raton, Fla., pages 100 et seq., U.S. Pat. Nos. 4,458,066, 4,500,707, 5,153,319, 5,869,643 and European patent application, EP 0294196, and elsewhere. The phosphoramidite and phosphite triester approaches are most broadly used, but other approaches include the phosphodiester approach, the phosphotriester approach and the H-phosphonate approach. The substrates are typically functionalized to bond to the first deposited monomer. Suitable techniques for functionalizing substrates with such linking moieties are described, for example, in Southern, E. M., Maskos, U. and Elder, J. K., Genomics, 13, 1007–1017, 1992.

In the case of array fabrication, different monomers and activator may be deposited at different addresses on the substrate during any one cycle so that the different features of the completed array will have different desired biopolymer sequences. As explained above, one or more intermediate steps may be required in each cycle, such as the conventional oxidation, capping or blocking, deprotection of protecting groups or deblocking, and washing steps in the case of in situ fabrication of polynucleotide arrays; again, these steps may be performed in flooding procedure.

As is well known in the art of ink jet printing, the amount of fluid that is expelled in a single activation event of a pulse jet can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to about 1000 pL, usually about 0.5 to about 500 pL and more usually about 1.0 to about 250 pL. A typical velocity at which the fluid is expelled from the chamber is more than about 1 m/s, usually more than about 10 m/s, and may be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities.

The spots can have widths (such as, for example, diameter for a round spot) in the range from a minimum of about 10 $\mu$m to a maximum of about 1.0 cm. In embodiments where very small spot sizes or feature sizes are desired, material can be deposited in small spots whose width is in the range about 1.0 $\mu$m to about 1.0 mm, usually about 5.0 $\mu$m to about 500 $\mu$m, and more usually about 10 $\mu$m to 200 $\mu$m.

In the method in accordance with the present invention, a reagent for forming the chemical compounds, such as, for example, a nucleotide reagent or a polynucleotide reagent, is deposited on the surface of the support as discussed above. Usually, a deposition sequence is initiated to deposit the desired fluid droplets containing nucleotide reagents on the surface of a support to provide dried drops on the surface according to the predetermined arrangement of the target, each with respective target locations and dimensions. In this sequence a processor causes a positioning system to position a head facing the surface of the support at an appropriate distance from the surface. The processor then causes the positioning system to scan the head across the surface line by line (or in some other desired pattern), while coordinating activation of the ejectors in the head so as to dispense droplets in accordance with the target pattern. If necessary or desired, the processor can repeat the load and dispensing sequences one or more times until the head has dispensed the desired number of droplets in accordance with the particular reaction step of the array formation. The number of drops dispensed in any one reaction step can be, for example, from about 1 to about 10, usually, about 3 to about 5. The total number of spots on the surface of the support may be, for example, at least about ten, at least about one hundred, at least about one thousand, or at least about one hundred thousand.

At the conclusion of the droplet dispensing for the reaction step, a determination is made as to whether one or more errors occurred during the deposition step. If during the deposition sequence all droplets were correctly deposited, they would yield the predetermined arrangement of target polynucleotides on the surface of the support. In practice, however, an error may occur in the deposition, which would result in an incorrect array pattern. Prior to the present invention supports having errors of the sort described above were discarded.

The nature of the determination as to whether an error has occurred in the deposition of the reagents depends on the nature of the error. The error may be a misfire of a nozzle, e.g., ink jet head, delivering a reagent to a spot or multiplicity of spots on the surface of a support. Other errors include, for example, electronic error (e.g., inkjet controller), artifact on surface of support, build up of material on inkjet head, satellite formation from nozzle, etc. At any layer represented by the depositing of reagents in one step of a sequence of steps, two groups of features may be formed in the event of a misprint due to an error. One group of features may have received necessary reagents and the coupling of the reagent to the growing molecule at various features on the support is successfully carried out. Another group of features may not have received necessary reagents and, therefore, any coupling reactions would be incomplete. If the subsequent steps of the synthesis (such as in this example washing of the surface, oxidation, washing, deblocking and washing) are carried out, various features on the surface will be incorrect. If the subsequent steps of the synthesis also contain the optional capping step, various features on the surface will be terminated and unusable in hybridization experiments.

In accordance with the present invention, a determination is made as to whether an error occurred in a particular cycle. The occurrence of an error may be determined by the use of an inspection station having an imaging system, which includes a camera to capture one or more images of the surface of a support on which the deposited droplets have dried to form spots. The camera is mounted for movement to facilitate image capture across the entire surface of the support although a suitable, camera could be located in a fixed position if desired. However, since high resolution images are usually required from the camera, and since a typical substrate may be about 12 inches by 12 inches, the camera will not likely be able to yield images of the required resolution of all arrays on a given support simultaneously. Thus, precision movement of the camera may be required. Of course, the light sensor of a camera could potentially be mounted elsewhere, with a light-receiving element (such as a mirror) mounted for movement and arranged to direct light to the sensor (using other moving and/or stationary mirrors, for example). Any suitable analog or digital image capture device (including a line by line scanner) can be used as the camera, although, if an analog camera is used, the processor should include a suitable analog/digital converter. In addition, more than one camera can be used if desired.

The support may have any desired dimension. However, the camera usually should have sufficient resolution to permit it to distinguish and observe each spot on the surface of the support. Movement of the camera with a moving device such as, e.g., a head retainer, facilitates it scanning over the entire surface of the support and its capturing of multiple images with sufficient resolution such that a good image of each spot of each array is obtained. The camera should have a resolution that provides a pixel size of about 1 to about 100 micrometers and more typically about 4 to about 10 micrometers.

Figure 4:
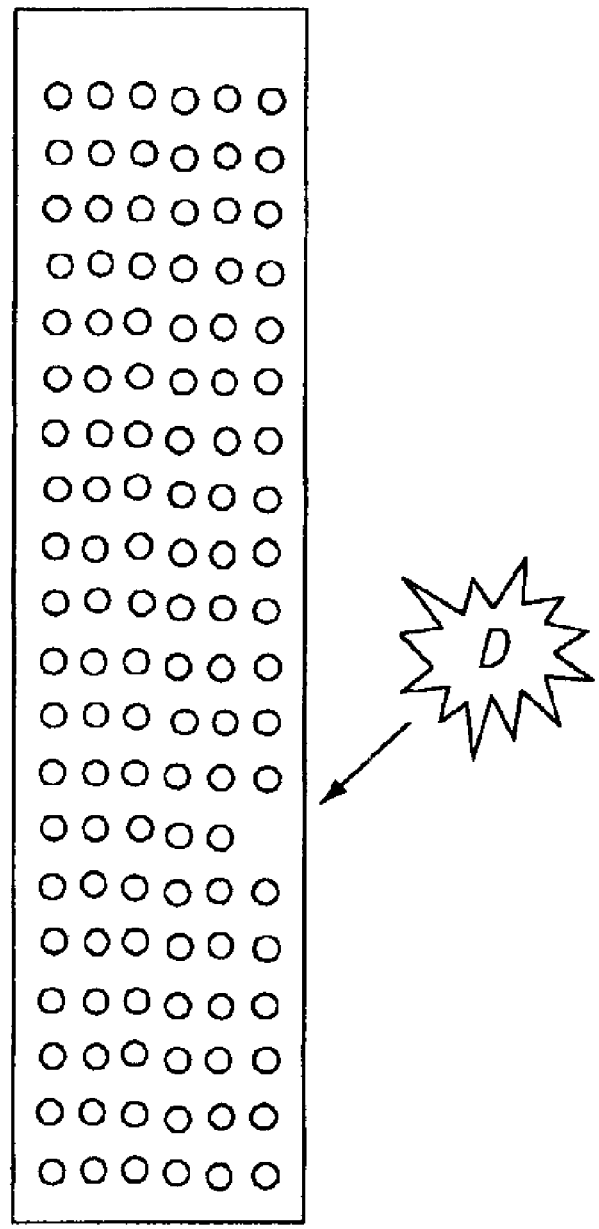
FIG. 4 is a depiction of a surface of a support having numerous features printed thereon and containing a missing feature due to a printing error.

In addition to imaging and analysis of every active feature after printing, a print test may be performed. During a print test, reagents from all nozzles and from all print heads are printed in close proximity on a solid support. The test print area is consequently imaged and analyzed for missing features. In the case where one or several features are missing, such as in the example shown in FIG. 4, the identity of the misfiring nozzle(s) may be inferred from the relative position of the missing feature on the support. Appropriate action on the malfunctioning nozzle(s) may be taken. The advantage of the test print over imaging of all features is the rapidity by which malfunctioning nozzles are diagnosed.

The images from the camera are observed after each cycle in the reaction scheme to determine whether an error has occurred in the deposition of the reagents. If an error is detected, then, in accordance with the present invention, the printing process is stopped and the support is treated to stabilize precursors of the chemical compounds on its surface. The nature of the stabilization of the precursors is dependent on the nature of the precursors. For example, the precursors may be addition polymers of monomeric units such as nucleotides and the reaction scheme utilizes phosphoramidite chemistry. In accordance with the reaction scheme, in any one cycle the precursors on the surface of the support are oxidized, as discussed above, to yield, e.g., a phosphate from a phosphite. In such a situation, the precursors that have been successfully printed usually have a protecting group. On the other hand, the precursors in the spots where an error has occurred usually have no protecting group since the surface was primed for reaction with the reagents delivered in a particular cycle.

In accordance with one aspect of the present invention, when an error is identified, the support is isolated from the printing chamber and treated to stabilize the material on the surface of the support. In the phosphoramidite coupling method of preparing polynucleotides, stabilization of the surface of the support may be achieved by simply washing the surface with, for example, acetonitrile. The primary consideration with respect to the stabilization of the materials on the surface of the support is that the materials on the surface be protected from any significant degradation, which might result in an incorrect array arrangement. To provide further protection in the stabilization step in the phosphoramidite coupling method, the surface of the support may be subjected to an oxidation step, i.e., oxidizing the materials, under conditions that do not result in cleavage of any protecting groups present. The oxidizing step may be carried out prior to or after a washing step in a manner similar to the oxidation step in the synthetic scheme. In one exemplary approach, the surface of the support may be subjected to an oxidation step followed by two separate wash steps, usually, with acetonitrile although other suitable wash solutions as mentioned below may be employed depending on the nature of the oxidation step. Alternatively, the surface of the support may be washed, subjected to an oxidation step and then washed again. Other approaches may also be employed. Following a wash step, whether or not employed in conjunction with an oxidation step, the surface of the support may be dried as is known in the art. No capping or deprotection of protecting groups is normally performed during the stabilization steps.

As indicated above, as part of the reaction scheme the precursors at the spots on the surface of the support have been deprotected as part of the synthesis cycle. Thus, the precursors are reactive to the reagents deposited on the surface during the cycle in question. Accordingly, reagents successfully deposited at spots on the surface react with the material at the specific locations on the surface of the support and the resultant product has a protecting group present due to the presence of a protecting group on the reagent that has been deposited. Thus, the resultant products at those spots where a successful deposition has occurred have a protecting group and an oxidation step does not affect such materials. On the other hand, spots where reagents were not successfully deposited have materials that do not have a protecting group, which was removed prior to the particular deposition step. Accordingly, the oxidation step results in oxidation of material at those spots where a reagent deposition step has failed.

Subsequent to the stabilization step, the support is then subjected to a cycle in the reaction scheme, which is the same as the cycle in which the error in deposition occurred. In other words the reagent applied in the cycle in which an error in deposition occurred is re-deposited on the surface. Reagents deposited at spots where the materials have a protecting group do not react with the material at those spots. Reagents deposited at spots that have materials with no protecting groups react with the materials at those spots. In this way the particular cycle in the reaction scheme is completed even though an error had occurred, and the remainder of the cycles in the reaction scheme may then be completed to yield the chemical compounds at the feature sites. In accordance with the present invention, an examination is made during each cycle to determine whether an error has occurred in the deposition step and the procedure discussed above is repeated to compensate for such errors when detected. Thus, after error detection and correction, the synthesis is continued in its normal pattern wherein subsequent reagents for forming the chemical compounds are deposited on the surface. The above steps are repeated until the chemical compounds are formed.

As mentioned above, the steps of capping, oxidation and deprotection can be accomplished by treating the entire surface of a support with a layer of the appropriate reagent, which is often referred to as a flooding step. Some or all of the above steps may be performed using flow cells. Accordingly, for example, after addition of a nucleoside monomer, such as depositing the reagent using an ink jet method, the support is placed into a chamber of a flow cell, which is typically a housing having a reaction cavity or chamber disposed therein. The flow cell allows fluids to be passed through the chamber where the support is disposed. The support may be mounted in the chamber in or on a holder. The housing usually further comprises at least one fluid inlet and at least one fluid outlet for flowing fluids into and through the chamber in which the support is mounted. In one approach, the fluid outlet may be used to vent the interior of the reaction chamber for introduction and removal of fluid by means of the inlet. On the other hand, fluids may be introduced into the reaction chamber by means of the inlet with the outlet serving as a vent and fluids may be removed from the reaction chamber by means of the outlet with the inlet serving as a vent.

The inlet of the flow cell is usually in fluid communication with an element that controls the flow of fluid into the flow cell such as, for example, a manifold, a valve, and the like or combinations thereof. This element in turn is in fluid communication with one or more fluid reagent dispensing stations. In this way different fluid reagents for one step in the synthesis of the chemical compound may be introduced sequentially into the flow cell. These reagents may be, for example, wash fluids, oxidizing agents, reducing agents, blocking or protecting agents, unblocking (deblocking) or deprotecting agents, and so forth. Any reagent that is normally a solid reagent may be converted to a fluid reagent by dissolution in a suitable solvent, which may be a protic solvent or an aprotic solvent. The solvent may be an organic solvent such as, by way of illustration and not limitation, organic solvents of from 1 to about 6, more usually from 1 to about 4, carbon atoms, including alcohols such as methanol, ethanol, propanol, etc., ethers such as tetrahydrofuran, ethyl ether, propyl ether, etc., acetonitrile, dimethylformamide, dimethylsulfoxide, and the like. In some circumstances, the solvent may be an aqueous medium that is solely water or may contain a buffer, or may contain from about 0.01 to about 80 or more volume percent of a cosolvent such as an organic solvent as mentioned above.

The amount of the reagents employed in each synthetic step in the method of the present invention is dependent on the nature of the reagents, solubility of the reagents, reactivity of the reagents, availability of the reagents, purity of the reagents, and so forth. Such amounts should be readily apparent to those skilled in the art in view of the disclosure herein. Usually, stoichiometric amounts are employed, but excess of one reagent over the other may be used where circumstances dictate. Typically, the amounts of the reagents are those necessary to achieve the overall synthesis of the chemical compound in accordance with the present invention. The time period for conducting the present method is dependent upon the specific reaction and reagents being utilized and the chemical compound being synthesized.

Using as an example the synthesis of polynucleotides on a surface by the phosphoramidite method, the step of oxidation to stabilize the surface of the support may be carried out in a dedicated flow cell. Accordingly, following addition of a monomer and discovery of an error in deposition, the support may be placed in the flow cell. Various fluid dispensing stations are connected by means of a manifold and suitable valves to the inlet of the flow cell. Each of the fluid dispensing stations contains a different fluid reagent involved in performing the particular steps involved in the stabilization procedure. Thus, in this example, one station may contain an oxidizing agent for oxidizing the phosphite to the phosphate and another station may contain a wash reagent such as acetonitrile.

As mentioned above, various approaches may be taken in carrying out the step for stabilizing the materials on the surface of a support once an error in deposition has been discovered. For example, the surface may be subjected to an oxidation step followed by consecutive wash steps. Accordingly, after the support has been isolated and moved to a flow cell, the oxidizing agent is allowed to pass into and out of the flow cell and the surface is then washed with the wash reagent as described above. After a drying step, the support is returned to the printing chamber where the surface is re-printed with the same reagent as in the mis-printing step. The normal repetition of cycles in the reaction scheme is then resumed.

After the printing step in any one cycle where no error in deposition was detected or where an error was detected and appropriate correction was made, the support may be removed from the printing chamber and subjected to steps for preparing the support for the printing step in a next cycle, i.e., dispensing of reagent for synthesizing the biopolymer. The steps for preparing the support for the next printing step depend on the method of synthesis. For example, where the phosphoramidite coupling method is employed, such steps include washing, optionally capping, oxidizing, deblocking or removal of a protecting group, and so forth. To this end in one approach the support is placed in a flow cell. Wash reagent is first allowed to pass into and out of the flow cell. Next, oxidizing agent is introduced into the flow cell. The support is then subjected to a deblocking step, which may be carried out in the same flow cell or a different flow cell. Accordingly, the support may be transported from a first flow cell to a second flow cell. At this point, a deblocking reagent for removing a protecting group is allowed to pass into and out of the second flow cell. The deblocking reagent is contained in a fluid dispensing station that is in fluid communication with the second flow cell. Next, wash reagent contained in a fluid dispensing station that is in fluid communication with the second flow cell is passed into and out of the second flow cell. Following the above synthetic steps, the support is transported from the second flow cell to the printing chamber where the next monomer addition in a subsequent cycle is carried out and the above repetitive synthetic steps are conducted as discussed above.

The following discussion is by way of illustration and not limitation. Referring to FIG. 1 a print step is carried out to place reagents on the surface of a support in predetermined locations. A determination is made as to whether an error occurred as a result of the failure of one or more of the printing elements involved in the printing process. If no error occurred, the support is subjected to, optionally a capping step, an oxidation step and a deblocking step as is customarily employed in phosphoramidite coupling. The support is then returned to the printing chamber for the next print step in the reaction scheme. The aforementioned sequence of steps is repeated. If the error determination indicates that a failure in the printing process occurred, the support is isolated and the surface is treated to stabilize the materials on the surface. Following stabilization, the support is subjected to the same printing step in which the error occurred. In other words the cycle in which the error occurred is repeated, i.e., the support is subjected to a re-printing step. Following the re-printing step, error determination is again carried out. Depending on the outcome of such determination, the appropriate sequence is followed as indicated in FIG. 1. As can be seen in FIG. 1, if an error is determined, the source of the error is repaired prior to the re-printing process.

As an alternative approach to that discussed above, it is within the purview of the present invention, to determine whether an error has occurred in any one cycle and then to reprint only those spots where an error in deposition occurred. In this approach a program is employed to ascertain which of the dispensing elements has caused an error. The program then activates a re-print cycle where the correct reagents are deposited in the locations where the failure to deposit reagents occurred. The support is then removed from the printing chamber and treated to stabilize the surface of the support as discussed above. The dispensing elements that caused the error are repaired. The reaction scheme is then resumed by beginning the next cycle in the addition of the monomer units.

Figure 2:
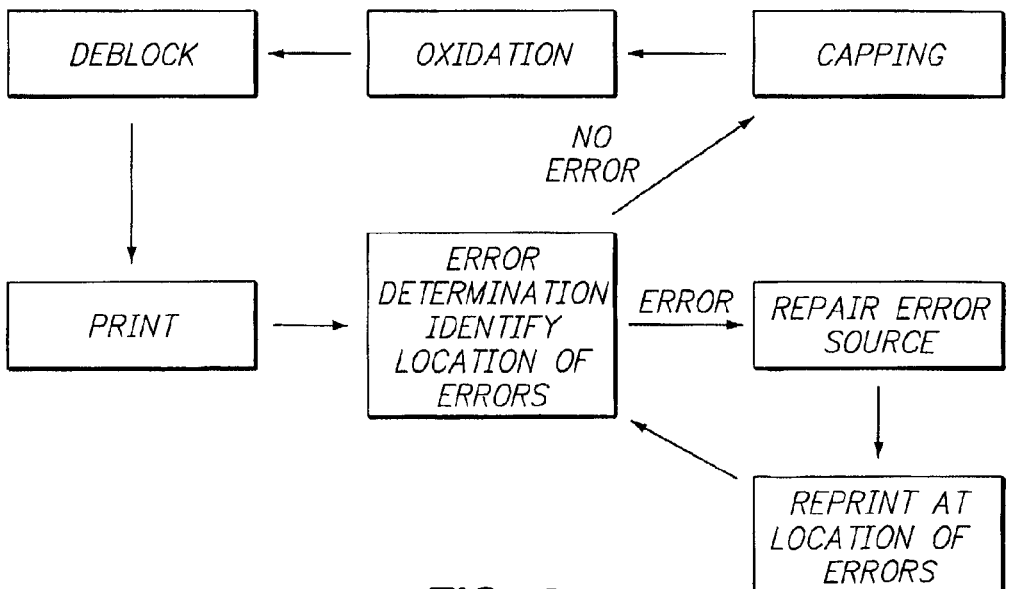
FIG. 2 is a flow chart depicting an alternative embodiment of a method in accordance with the present invention.

The aforementioned alternative approach is depicted as a flow chart in FIG. 2. Referring to FIG. 2 a print step is carried out to place reagents on the surface of a support in predetermined locations. A determination is made as to the occurrence and location of an error as a result of the failure of one or more of the printing elements involved in the printing process. If no error occurred, the support is subjected to, optionally a capping step, an oxidation step and a deblocking step as is customarily employed in phosphoramidite coupling. The support is then returned to the printing chamber for the next print step in the reaction scheme. The aforementioned sequence of steps is repeated. If the error determination indicates that a failure in the printing process occurred, the support is retained in the printing chamber and the support is subjected to the same printing step in which the error occurred where only the specific locations that were affected are re-printed. In other words the cycle in which the error occurred is repeated only for those specific locations. Following the re-printing step, error determination is again carried out. Depending on the outcome of such determination, the appropriate sequence is followed as indicated in FIG. 2. As can be seen in FIG. 2, if an error is determined, the source of the error is repaired prior to the re-printing process.

In yet another approach a print step is carried out and the printed features are then checked for errors. If errors are detected, all features are reprinted, that is, the missing features plus the ones that were deposited correctly.

Various apparatus may be employed in carrying out the present invention. One such apparatus comprises a platform and a plurality of flow cells mounted on the platform wherein one of the flow cells is dedicated to stabilization of supports on which errors have occurred in deposition of reagents. The flow cells comprise a chamber, a holder for the support, at least one inlet and an outlet, wherein each of the inlets is in fluid communication with a manifold. One or more fluid dispensing stations are mounted on the platform and are in fluid communication with one or more of the plurality of flow cells by means of the manifolds. A station for monomer addition to the surface of the support, for example, a station comprising one or more printing heads, is mounted on the platform. The apparatus also comprises a mechanism for moving a support to and from the station for monomer addition and a flow cell and from one flow cell to another flow cell. The mechanism may be, for example, a robotic arm, and so forth. The mechanism for moving a support is in communication such as, for example, electrical communication, with a mechanism for determining whether an error occurred in the deposition of reagents in the station for monomer addition. As a result of such communication, the mechanism for moving the support may be activated to move the support from the reaction chamber to a stabilization chamber that is dedicated to subjecting the support to stabilizing reagents.

In an alternative embodiment of an appropriate apparatus in accordance with one aspect of the present invention, a dedicated stabilization chamber is not employed. The apparatus comprises a mechanism for activating only those dispensing elements, e.g., print heads, which were determined to have resulted in an error in the deposition of the reagents. Thus, once a determination of an error is made, the dispensing elements that caused the error in deposition are repaired or replaced. Next, reagents of the cycle in which an error occurred are dispensed only to the sites on the support at which incorrect deposition was detected. Accordingly, the dispensing elements may be activated to dispense only those reagents that were not dispensed or incorrectly dispensed to locations on the support in the step of the synthesis in question. Such a mechanism comprises, in one exemplary approach, loading the printing pattern for the step of the synthesis in question (reagent vs. position map), masking out the positions that were dispensed correctly, and re-printing the step using the masked pattern.

In one embodiment of a mechanism for moving a support from one flow cell to another flow cell or from the print chamber to a flow cell or a stabilization flow cell, the support is delivered into the opening in the wall of the flow cell housing by engagement with a holding element, which usually comprises a main arm and an end portion that contacts and engages a surface of the support. In one embodiment the holding element is in the form of a fork that is vacuum activated. Other embodiments of the holding element include, for example, grasping elements such as movable finger-like projections, and the like. The holding element is usually part of a transfer robot that comprises a robotic arm that is capable or transferring the support from various positions where steps in the synthesis of the chemical compound are performed such as between several flow devices in accordance with the present invention. In one embodiment a transfer robot is mounted on the main platform. The transfer robot may comprise a base, an arm that is movably mounted on the base, and an element for holding the support during transport that is attached to the arm. Also included is a controller for controlling the movement of the mechanism.

Figure 3:
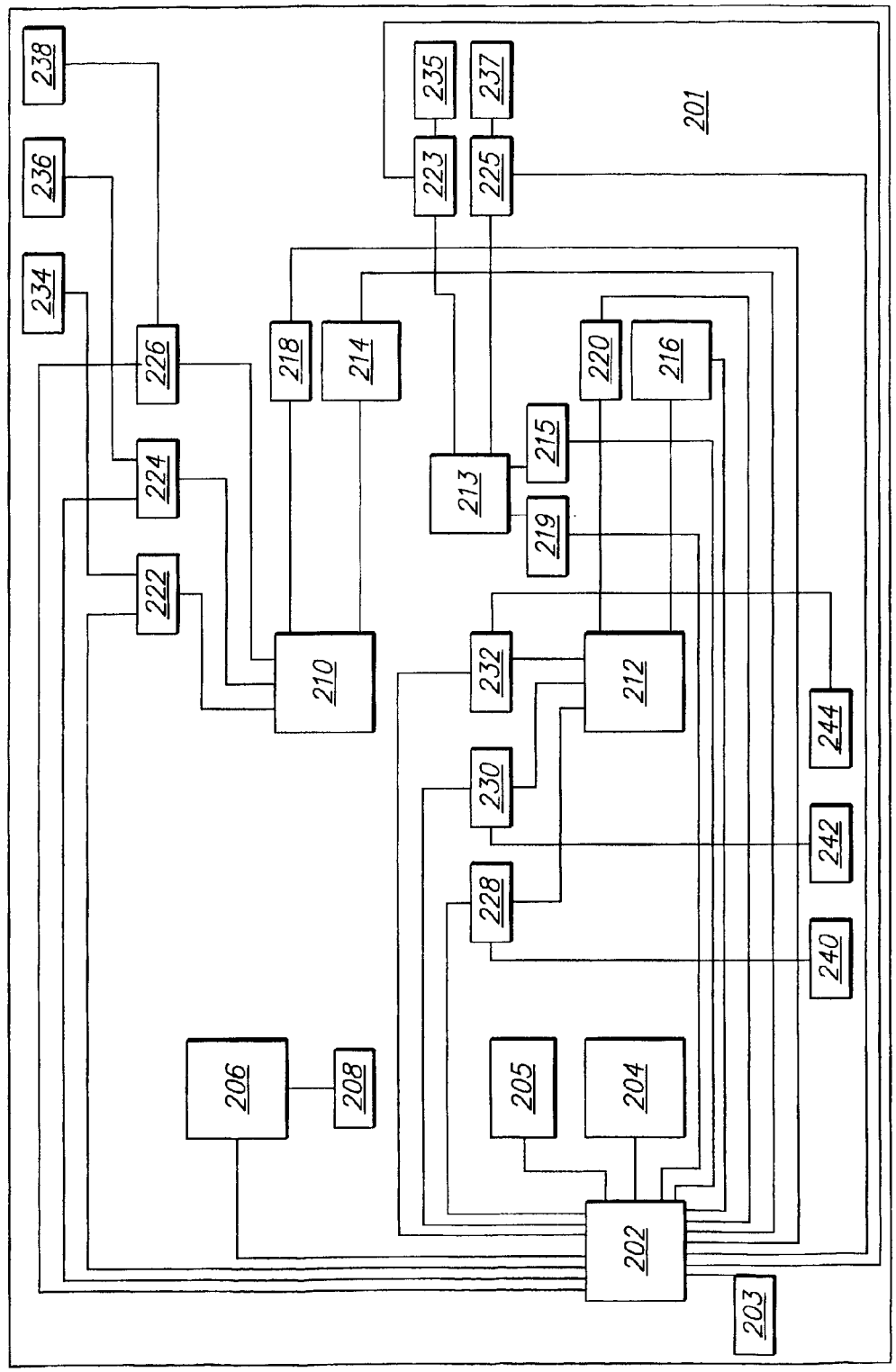
FIG. 3 is a schematic diagram depicting an embodiment of an apparatus in accordance with the present invention.

One embodiment of an apparatus in accordance with the present invention is depicted in FIG. 3 in schematic form. Apparatus 200 comprises platform 201 on which the components of the apparatus are mounted. Apparatus 200 comprises main computer 202, with which various components of the apparatus are in communication. Video display 203 is in communication with computer 202. Apparatus 200 further comprises print chamber 204, which is controlled by main computer 202. The nature of print chamber 204 depends on the nature of the printing technique employed to add monomers to a growing polymer chain. Such printing techniques include, by way of illustration and not limitation, inkjet printing, and so forth. Camera 205 is in communication with main computer 202. Transfer robot 206 is also controlled by main computer 202 and comprises a robot arm 208 that moves a support to be printed from print chamber 204 to first flow cell 210 or second flow cell 212 or stabilization flow cell 213. In one embodiment robot arm 208 introduces a support into print chamber 204 horizontally for printing on a surface of the support and introduces the support into a flow cell vertically. First flow cell 210 is in communication with program logic controller 214, which is controlled by main computer 202, and second flow cell 212 is in communication with program logic controller 216, which is also controlled by main computer 202. First flow cell 210 is in communication with flow sensor and level indicator 218, which is controlled by main computer 202, and second flow cell 212 is in communication with flow sensor and level indicator 220, which is also controlled by main computer 202. First flow cell 210 is in fluid communication with manifolds 222, 224 and 226, each of which is controlled by main computer 202 and each of which is in fluid communication with a source of fluid reagents, namely, 234, 236 and 238, respectively. Second flow cell 212 is in fluid communication with manifolds 228, 230 and 232, each of which is controlled by main computer 202 and each of which is in fluid communication with a source of fluid reagents, namely, 240, 242 and 244, respectively. Stabilization flow cell 213 is in communication with program logic controller 215, which is controlled by main computer 202, and is in communication with flow sensor and level indicator 219, which is controlled by main computer 202. Stabilization flow cell 213 is in fluid communication with manifolds 223 and 225, each of which is controlled by main computer 202 and each of which is in fluid communication with a source of fluid reagents, namely, 235 and 237, respectively.

The apparatus of the invention further comprise appropriate electrical and mechanical architecture and electrical connections, wiring and devices such as timers, clocks, and so forth for operating the various elements of the apparatus. Such architecture is familiar to those skilled in the art and will not be discussed in more detail herein.

The methods in accordance with the present invention may be carried out under computer control, that is, with the aid of a computer. For example, an IBM® compatible personal computer (PC) may be utilized. The computer is driven by software specific to the methods described herein. A preferred computer hardware capable of assisting in the operation of the methods in accordance with the present invention involves a system with at least the following specifications: Pentium® processor or better with a clock speed of at least 100 MHz, at least 32 megabytes of random access memory (RAM) and at least 80 megabytes of virtual memory, running under either the Windows 95 or Windows NT 4.0 operating system (or successor thereof).

Software that may be used to carry out the methods may be, for example, Microsoft Excel or Microsoft Access, suitably extended via user-written functions and templates, and linked when necessary to stand-alone programs that perform other functions. Examples of software or computer programs used in assisting in conducting the present methods may be written, preferably, in Visual BASIC, FORTRAN and $C^{++}$. It should be understood that the above computer information and the software used herein are by way of example and not limitation. The present methods may be adapted to other computers and software. Other languages that may be used include, for example, PASCAL, PERL or assembly language.

A computer program may be utilized to carry out the above method steps. The computer program provides for (i) placing a support into a chamber for printing a predetermined arrangement of features on the surface of the support, (ii) dispensing reagents for a specific cycle of chemical reactions involved in the synthesis of compounds at the feature sites, (iii) activating a mechanism for determining the occurrence of an error in the deposition of reagents, (iv) either (a) if an error is detected, moving the support to a stabilization chamber and subsequently moving the support to a printing chamber to re-print the entire surface or, if no error is detected, moving the support to a chamber for flooding of the support surface with a reagent involved in the synthesis of the chemical compounds or (b) identifying features on the support that were not printed correctly and re-printing only those features, (v) removing the support from the housing chamber, (vi) placing the support into a chamber of a flow device, (vii) introducing a fluid reagent for conducting a reaction step into the reagent chamber, (viii) removing the fluid reagent from the reagent chamber, (ix) removing the support from the housing chamber and (x) moving the support to the printing chamber to conduct the next cycle in the synthesis of the chemical compound.

The computer program may be carried on a program product which includes a computer readable storage medium having a computer program stored thereon and which, when loaded into a programmable processor, provides instructions to the processor of that apparatus such that it will execute the procedures required of it to perform a method of the present invention. The computer readable storage medium may be an optical, magnetic, or solid state memory, any of which may be portable or fixed.

Another aspect of the present invention is a computer program product comprising a computer readable storage medium having a computer program stored thereon which, when loaded into a computer, performs the aforementioned method.

Following receipt by a user of an array made by an apparatus or method of the present invention, it will typically be exposed to a sample (for example, a fluorescent-labeled polynucleotide or protein containing sample) and the array is then read. Reading of the array may be accomplished by illuminating the array and reading the location and intensity of resulting fluorescence at each feature of the array. For example, a scanner may be used for this purpose where the scanner may be similar to, for example, the AGILENT MICROARRAY SCANNER available from Agilent Technologies Inc, Palo Alto, Calif. Other suitable apparatus and methods are described in U.S. patent applications Ser. No. 09/846,125 "Reading Multi-Featured Arrays" by Dorsel, et al.; and Ser. No. 09/430,214 "Interrogating Multi-Featured Arrays" by Dorsel, et al. The relevant portions of these references are incorporated herein by reference. However, arrays may be read by methods or apparatus other than the foregoing, with other reading methods including other optical techniques (for example, detecting chemiluminescent or electroluminescent labels) or electrical techniques (where each feature is provided with an electrode to detect hybridization at that feature in a manner disclosed in U.S. Pat. No. 6,221,583 and elsewhere). Results from the reading may be raw results (such as fluorescence intensity readings for each feature in one or more color channels) or may be processed results such as obtained by rejecting a reading for a feature that is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing).

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for synthesizing an array of biopolymers, selected from the group consisting of polynucleotides and polypeptides, on the surface of a support wherein said synthesis comprises a plurality of steps wherein reagents for forming said biopolymers are deposited on the surface of the support and wherein on or more of said plurality of steps may comprises an error in said deposition, said method comprising:
   (a) placing a support having a functionalized surface into a reaction chamber,
   (b) dispensing, to multiple locations on said surface from a plurality of nozzles, a plurality of drops of a reagent for forming said biopolymers,
   (c) repeating steps (a) and (b) in one or more cycles so as to form said biopolymers, wherein the reagents deposited in different cycles at the same locations on said surface may or may not be the same;

the method additionally comprising in at least one selected cycle, (d) determining, using an imaging system, whether an error occurred in the dispensing of said reagent in the selected cycle, said error arising from the failure of one or more nozzles to dispense said reagents to one or more of said multiple locations, (e) if an error occurred,
(i) isolating said support,
(ii) stabilizing the surface of said support in said holding chamber,
(iii) correcting the source of said error, and
(iv) dispensing, to said surface from a plurality of nozzles, a plurality of drops of said reagent for the cycle in which the error occurred, and (f) subjecting said support to reagents for preparing said support for a subsequent dispensing step.

2. A method according to claim 1 wherein said error is determined by means of comparing an imprint of the delivered spots to a predetermined imprint.

3. A method according to claim 2 wherein said imprint of said delivered spots is determined by means of a camera.

4. A method according to claim 2 wherein said comparing is carried out by means of a computer.

5. A method according to claim 1 wherein said reagent for forming said biopolymers comprises a biopolymer subunit.

6. A method according to claim 1 wherein said cycles comprise the steps of blocking and deblocking.

* * * * *

UNITED STATES PATENT AND TRADEMARK OFFICE
CERTIFICATE OF CORRECTION

PATENT NO. : 6,939,673 B2
DATED : September 6, 2005
INVENTOR(S) : Bass et al.

It is certified that error appears in the above-identified patent and that said Letters Patent is hereby corrected as shown below:

Title page,
Item [56], References Cited, OTHER PUBLICATIONS,
"U.S. Appl. No. 09/359,527," reference, delete "Web" and insert -- Webb --.
Item [57], ABSTRACT,
Line 2, delete "purality" and insert -- plurality --.
Line 4, after "deposited" delete "o" and insert -- on --.

Column 22,
Line 56, after "wherein" delete "on" and insert -- one --.
Line 57, delete "comprises" and insert -- comprise --.

Signed and Sealed this

Twenty-first Day of March, 2006

JON W. DUDAS
*Director of the United States Patent and Trademark Office*